United States Patent [19]

Kirsch

[11] Plant 5,197

[45] Feb. 28, 1984

[54] LILY NAMED FREEDOM

[75] Inventor: Ted T. Kirsch, Myrtle Point, Oreg.

[73] Assignee: Sun Valley Bulb Farms, Inc., Myrtle Point, Oreg.

[21] Appl. No.: 422,202

[22] Filed: Sep. 23, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct variety of lily plant of the Parkmanni-type Oriental Hybrid particularly distinguished by its large 7 to 8 inch white, downwardly and outwardly projecting saucer-shaped flowers which are borne in a raceme arrangement on long, strong stems and outwardly-projecting pedicels, usually with one bud or flower on each pedicel, and by its green, glossy, and relatively disease-resistant foliage.

2 Drawing Figures

BACKGROUND OF THE NEW PLANT

This new variety of lily plant originated as a seedling of unknown parentage discovered by me among field grown plants at my nursery in Arcata, Calif. The relatively disease-resistant, glossy green foliage and large white flowers prompted me to select this new plant for propagation and study, with the result that I have found advantageous and distinctive characteristics in the new plant which make it a valuable addition to the field of commercial lily culture for cut flower production. Propagation of this new lily at Arcata, Calif. through successive generations by means of scales and tissue culture has shown that its distinctive characteristics hold true from generation to generation and appear to be firmly fixed.

DESCRIPTION OF THE DRAWING

This new variety of lily plant is illustrated by the accompanying photographic drawing which in full color shows a full grown blooming plant in the upper view and a close-up of a bloom in the lower view. The color rendition is as nearly true as can be obtained by conventional photographic procedures.

DESCRIPTION OF THE NEW PLANT

The following is a detailed description of my new variety of lily plant as observed at Arcata, Calif., in the spring of 1982, the observations having been made on greenhouse-grown plants and the color designations being according to the R.H.S. Colour Chart published by The Royal Horticultural Society of London, England.

THE PLANT

Origin: Seedling.
Parentage: Unknown.
Classification: Oriental Hybrid, Parkmanni.
Form: A tall single stem from each bulb.
Height: About 2½ to 3½ feet at maturity.
Growth: Sturdy and upright with excellent strength.
Cane size: From ¼ inch in diameter for a small bulb to ½ inch in diameter for a large bulb.
Foliage:
- *At flower cluster.*—Two in number on each pedicel, with one at the base of the pedicel being about 6 to 7 inches long and 1¾ to 2 inches wide, and another located on the pedicel about 1¾ inches from the flower and being 3½ to 5½ inches long and ⅞ to 1½ inches wide.
- *Shape.*—Lanceolate.
- *Texture.*—Leathery.
- *Aspect.*—Smooth.
- *Ribs and veins.*—Distinct, parallel veins from base to tip.

Bulblets:
- *Occurrence.*—One to three on underground stem on each healthy, normal plant at digging time.
- *Size.*—From ¼ inch to 1 inch in diameter.
- *Color.*—White, with occasional pink shading at tips.

Bulbs:
- *Size.*—From ½ inch to 12 inches in circumference, depending on age.
- *Color.*—White, with yellow and pink overtones. As the bulbs become older, the overtones of yellow and pink become more and more prominent.

THE BUD

Form: Lanceolate, with acute apex.
Size: Averaging about 5 to 6 inches long and 1¼ to 1½ inches in diameter.
Number: Usually one on each pedicel, with 1 to 10 pedicels on a plant, according to culture and bulb size.
Opening: Normal, with buds opening successively from the lowermost bud to the top bud, which is the last to open.
Color: White, with a midrib of faint light green color, and some reddish coloration on the upwardly-facing petal sides.
Surface: Rugose, leathery, with prominent veins.
Pedicel: Strong and generally outfacing, being angled about 60° from the vertical, with buds slightly downfacing.
- *Color.*—Light green underneath and dark maroon on top; glabrous and glaucous.
- *Length.*—About 4 to 5 inches.

THE FLOWER

Blooming habit: Annually, blooming profusely outdoors in July. Under normal lily forcing conditions and temperatures the plant blooms in 100 to 110 days.

Size of flower: Large, averaging about 8 inches in diameter.

Borne: From larger bulbs the inflorescence has a raceme arrangement with each pedicel bearing one bud. The size of the bulb and its cultural care will determine the number of blooms and buds to be found on any given inflorescence. From large bulbs, this lily may have 3 to 6 blooms open at one time.

Shape: Generally bow-shaped, with uniformly-spaced petals in a star arrangement, and the outer ⅓ of each petal curving backwardly.

Petalage: Normal, three petals and three sepals.

*Form.*—Lanceolate with obtuse apex (sepals have acuminate apex) and with a center furrow bisecting each petal longitudinally. The edges of the petals undulate slightly, the edges of sepals more so.

*Size.*—Petals are about 5½ to 6 inches long and about 2½ inches wide.

*Color.*—Upper side: Upon opening, the petal is R.H.S. White 155-D. The base of the midrib (nectary) is light green for about 1½ inches. The basal ⅔ of the petal is covered with numerous white or maroon spots. The maroon spots fade to white as the flower ages. Under side: R.H.S. White 155-D. There is some red coloration on the sides of the petals facing upwardly which fades away as the flower ages.

*Papillae.*—Present at the base of the petal, 10 to 20 in number, and associated with the spots.

*Aspect.*—Velvety.

Fragrance: Sweet.

Discoloration: The color lightens as the petal becomes more transparent (less opaque) due to aging.

Effect of weather: The flower generally is not affected by weather but will age as temperature rises.

Persistence: The flower tends to hang on and dry.

Lasting quality: On the plant, two to three weeks depending on the size of the bulb and its environmental temperature. As a cut flower, 10 to 14 days.

REPRODUCTIVE ORGANS

Stamens: Six in number, orderly arrangement around the pistil.

*Anthers.*—R.H.S. Greyed Orange 169-B, about one inch long.

*Filaments.*—About 3¾ inches long; white at base to green at tip.

Pistils:

*Number.*—1.

*Style.*—About 3¼ inches long and light green in color.

*Stigma.*—Purple in color.

*Ovary.*—Classified as a schizocarp, about 1½ inches long and 1 inch in diameter, dehiscing into thirds and containing six rows of seeds of the usual shape for lilies.

I claim:

1. A new and distinct variety of Oriental Hybrid lily plant substantially as herein shown and described, characterized by its large, white, downwardly and outwardly facing saucer-shaped flowers borne on strong, stiff, outwardly projecting pedicels, by petals that are lightly covered with maroon and white spots and have their outer one third portions recurved, by the glossy green and relatively disease-free foliage, and by the long lasting quality of the blooms whether on the plant or as cut flowers.

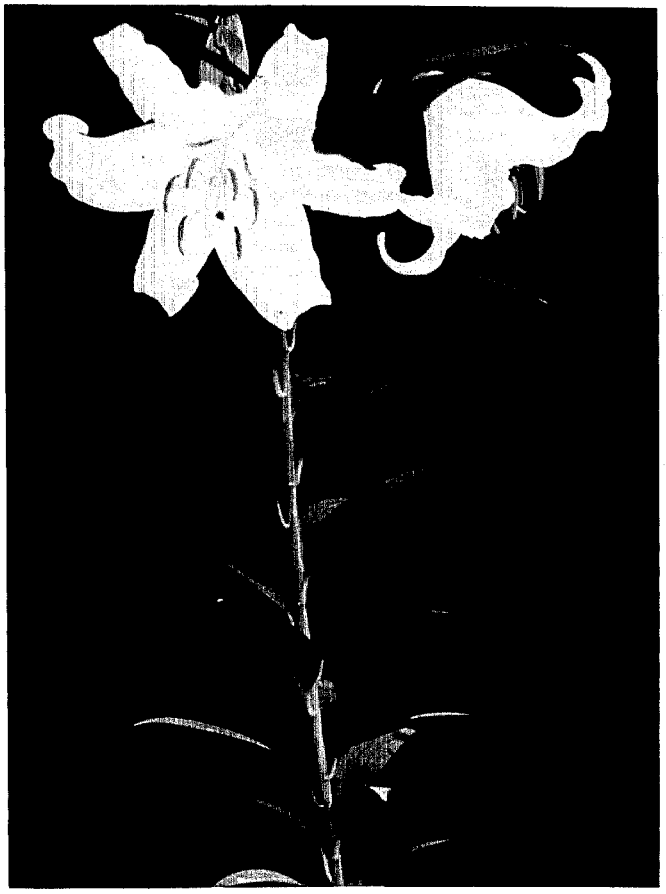
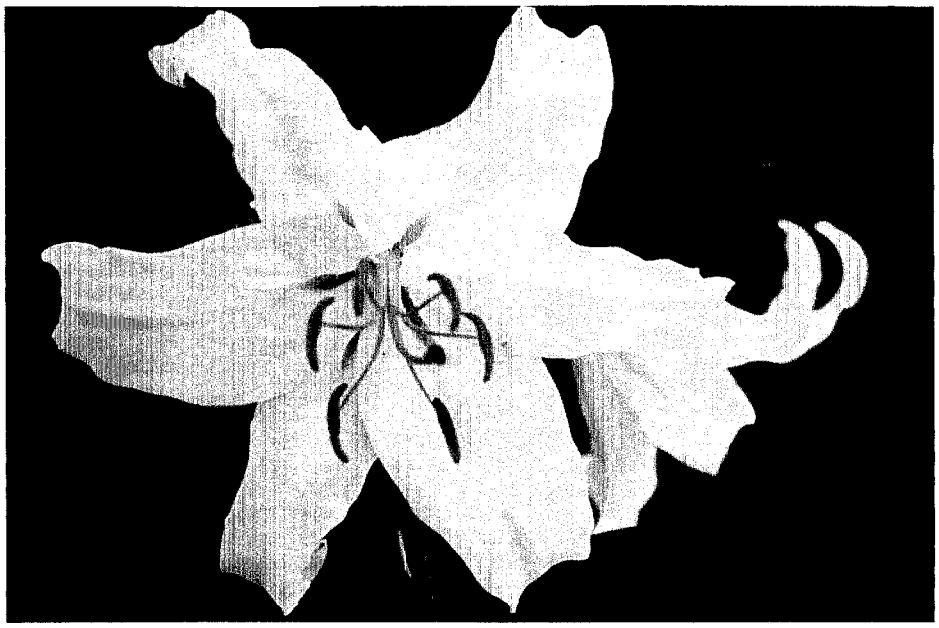

* * * * *